United States Patent [19]

Laghi

[11] Patent Number: 5,503,543
[45] Date of Patent: Apr. 2, 1996

[54] PROSTHETIC CASTING MACHINE

[76] Inventor: Aldo A. Laghi, 2400 Feathersound Dr., Apr. #1118, Clearwater, Fla. 34622

[21] Appl. No.: 314,983

[22] Filed: Sep. 29, 1994

[51] Int. Cl.$^6$ .............................. B28B 1/30; B28B 21/42
[52] U.S. Cl. .......................... 425/2; 425/389; 425/393; 264/222; 264/503; 264/571; 264/573; 264/DIG. 30; 623/27; 623/901
[58] Field of Search .............................. 425/2, 389, 392, 425/393, 111, 112, DIG. 14; 264/222, 223, DIG. 30, 501, 503, 511, 512, 515, 516, 526, 531, 532, 541, 550, 553, 554, 559, 560, 566, 573, 549, 571; 623/28, 29, 33–36, 901, 27; 249/165, 166

[56] References Cited

U.S. PATENT DOCUMENTS

| | | | |
|---|---|---|---|
| 980,457 | 1/1911 | Toles | 623/34 |
| 2,730,785 | 1/1956 | Williams | 249/165 |
| 3,200,442 | 8/1965 | Haller | 425/389 |
| 3,905,738 | 9/1975 | Farrell | 425/389 |
| 4,010,230 | 3/1977 | Repenning | 264/549 |
| 5,137,448 | 8/1992 | Dougherty et al. | 264/222 |
| 5,219,364 | 6/1993 | Lloyd | 623/33 |
| 5,314,497 | 5/1994 | Fay et al. | 623/34 |
| 5,380,481 | 1/1995 | Oberle | 264/550 |

*Primary Examiner*—Jay H. Woo
*Assistant Examiner*—Vi Duong Dang
*Attorney, Agent, or Firm*—Joseph C. Mason, Jr.; Ronald E. Smith

[57] ABSTRACT

A prosthetic casting machine receives an amputated stump while a patient is standing so that a hard socket can be made based upon the shape of the stump when it is under load. The machine includes a brim for accommodating an above-the-knee stump or a retaining disc for below-the-knee stumps. A telescoping leg enables precise adjustment of the height of the machine to accommodate patients of differing heights. The patient's stump is inserted into a liner and the liner is coated with plaster before the stump is inserted into the machine. After insertion, while the patient is standing, compressed air is introduced into a space between a transparent flexible bladder and a transparent rigid cylinder so that a uniform pressure is applied to the plaster by the bladder. The transparent parts enable a prosthetist to observe the results of the pressurization so that corrective steps may be taken if the plaster is not evenly compressed. The stump is elongated by a vacuum applied at its distal end and the plaster sets while the stump is elongated. This produces a hard socket having a clearance space between the distal end of the stump and the distal end of the socket.

20 Claims, 3 Drawing Sheets

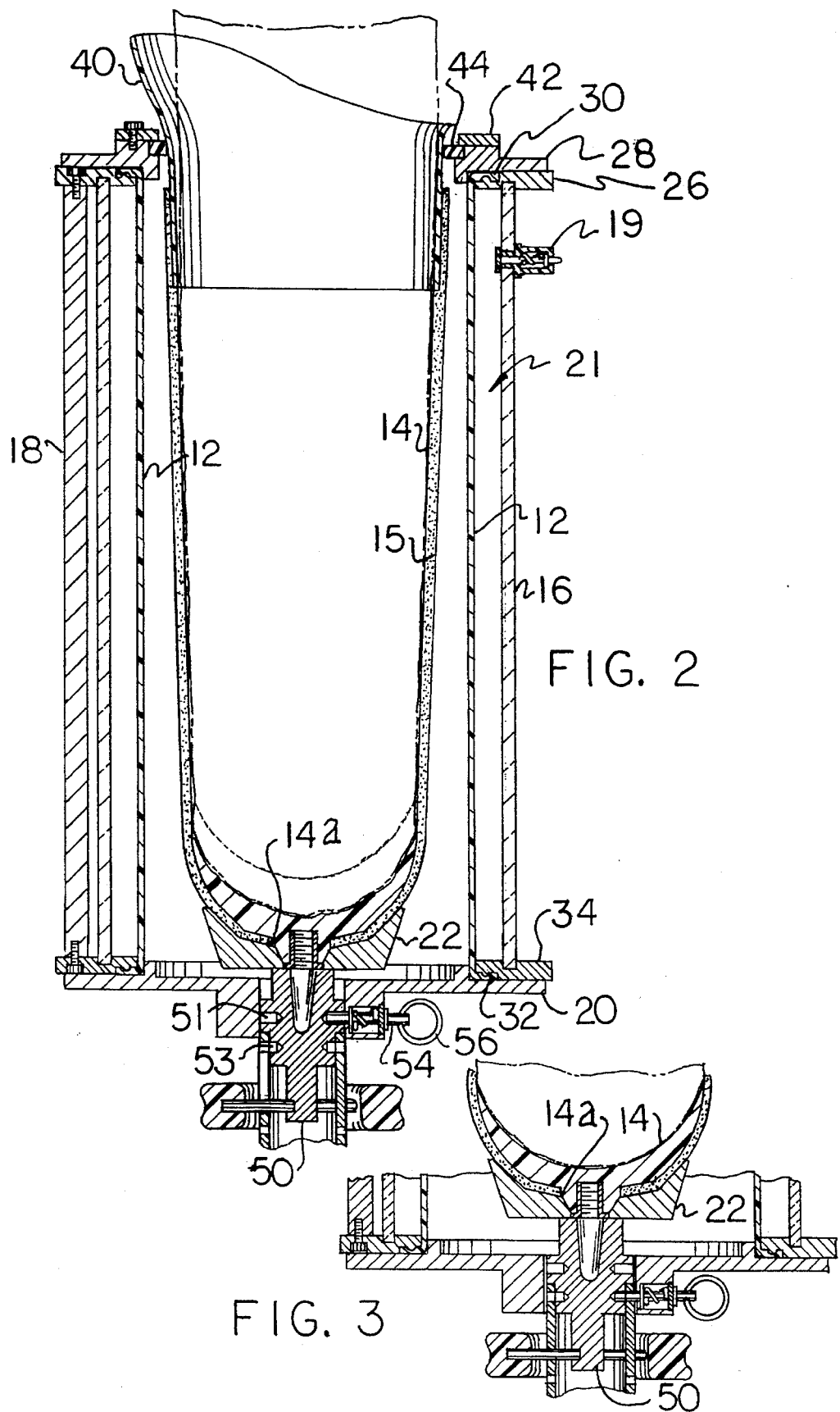

PROSTHETIC CASTING MACHINE

BACKGROUND OF THE INVENTION

1. Field of the Invention

This invention relates, generally, to prosthetic devices. More particularly, it relates to a machine for casting a prosthesis for a lower limb while the stump is under load.

2. Description of the Prior Art

Hard sockets for receiving an amputee patient's stump were originally hand carved from wood and lined with leather to soften the contact between the stump and the socket.

In more modern times, however, devices and methods have been developed that enable a prosthetist to fashion a socket that fits each individual patient. In one well known method, the stump is first inserted into a cushioned liner and the liner is wrapped in plaster. The prosthetist then applies manual pressure to conform the plaster and liner to the shape of the stump; the pressure is applied until the plaster sets. The stump is then removed from the plaster impression, and said impression is used to make a positive of the stump. The hard socket is then made from the positive, employing either casting of thermoset material, or vacuum or pressure forming of a thermoplastic sheet.

One drawback of the manual pressure method is that its success depends to a large degree upon the manual dexterity and skill of the prosthetist. Although a highly skilled prosthetist might be able to exert a nearly uniform pressure on all sections of the plaster, a perfectly fashioned impression is a rarity.

A machine that reduces the level of skill required of the prosthetist and which consistently applies a uniform pressure to the plaster includes a cylindrical bladder that ensleeves the patient's stump after plaster has been applied thereto. A uniform pressure is applied to the exterior of the bladder so that it is driven radially inwardly and transmits the uniform pressure to the plaster. Thus, the bladder supplants the hands of the prosthetist and the pressure is applied uniformly to all sections of the plaster. The result is a better fit than usually provided by the manual method described earlier.

However, both the manual and machine-aided methods described above have an important limitation; they work only when the patient is in a sitting or reclining position, i.e., when there is no load on the stump. Thus, the hard socket fits the stump well when the stump is not bearing the patient's weight, but the fit is not so precise when the stump is bearing weight. Moreover, the known device cannot accommodate above-the-knee amputees.

Still another drawback of the known device is that its bladder is opaque. This prevents the prosthetist from seeing how well the plaster is being pressed against the patient's stump. If the bladder were transparent, the prosthetist could observe the pressurizing process, and could note any locations where the bladder failed to provide the needed pressure on the plaster; corrective measures could then be taken.

The known devices are also deficient to the extent that they often cause discomfort to the amputee because they provide insufficient space at the distal end of the hard socket. Empty space at the distal end of the socket is needed because the stump may have jagged bone residue which cannot comfortably support weight.

What is needed, then, is a prosthetic casting machine having the capability of applying a uniform pressure to plaster that overlies a weight-bearing stump. Another need exists for a transparent bladder. A hard socket made by such a machine would fit the patient well even when the stump is bearing the patient's weight, and would provide an empty space at the distal end of the socket.

Such a casting machine is also needed for above-the-knee amputees.

However, in view of the prior art as a whole at the time the present invention was made, it was not obvious to those of ordinary skill in this art how an improved machine having the desired qualities could be built.

SUMMARY OF THE INVENTION

The prosthetic casting machine of this invention includes a transparent bladder of flexible, cylindrical configuration for ensleeving a plaster-covered liner that covers the residual limb of an amputee; the bladder is concentrically disposed with respect to the liner. A transparent cylinder is concentrically disposed with respect to and ensleeves the bladder. Means are provided for introducing a gaseous fluid into a cylindrical space between the bladder and cylinder and for evacuating said gaseous fluid from said cylindrical space. A distal rest plate supported by a support plate is disposed at a lowermost end of the bladder and cylinder, and a rigid, upstanding leg means supports said support plate and hence said distal rest plate so that the plaster-covered liner receiving a patient's stump is supported by the distal rest plate and the leg means so that a uniform pressure is applied to said plaster and liner upon introduction of said gaseous fluid into said space between said cylinder and bladder. Thus, the stump is under load when said pressure is applied. A unique "suck back" procedure elongates the stump until the plaster has set, thereby producing clearance space at the distal end of the hard socket that is produced from the plaster positive. After the plaster has set, the pressure is relieved and vacuum is applied to the space between the flexible bladder and the rigid cylinder to release the bladder from said plaster. The stump is then withdrawn and the plaster is cut longitudinally in the well-known way. The plaster impression is used to produce a positive of the stump in the conventional fashion and from that positive a hard socket is made. Unlike the hard sockets heretofore known, the hard socket produced by this machine matches the contour of the stump under load, and leaves a clearance space at the distal end of said socket.

A brim for receiving the residual limb of an above the knee amputee is also provided.

It is therefore clear that the primary object of this invention is to provide the first prosthetic casting machine that fashions a hard socket from a positive made while a patient's stump is under load.

Another important object is to provide such a machine that accommodates the residual limb of above-the-knee amputees.

Another object is to provide such a machine that produces hard sockets that have clearance space at their distal end so that the distal end of a patient's stump does not bear against said distal end of said socket.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 2 is a sectional view taken along line 2—2 in FIG. 1;

FIG. 3 is a sectional view like FIG. 2, depicting the novel apparatus in its "suck back" configuration.

DETAILED DESCRIPTION OF THE PREFERRED EMBODIMENT

Figure 1:
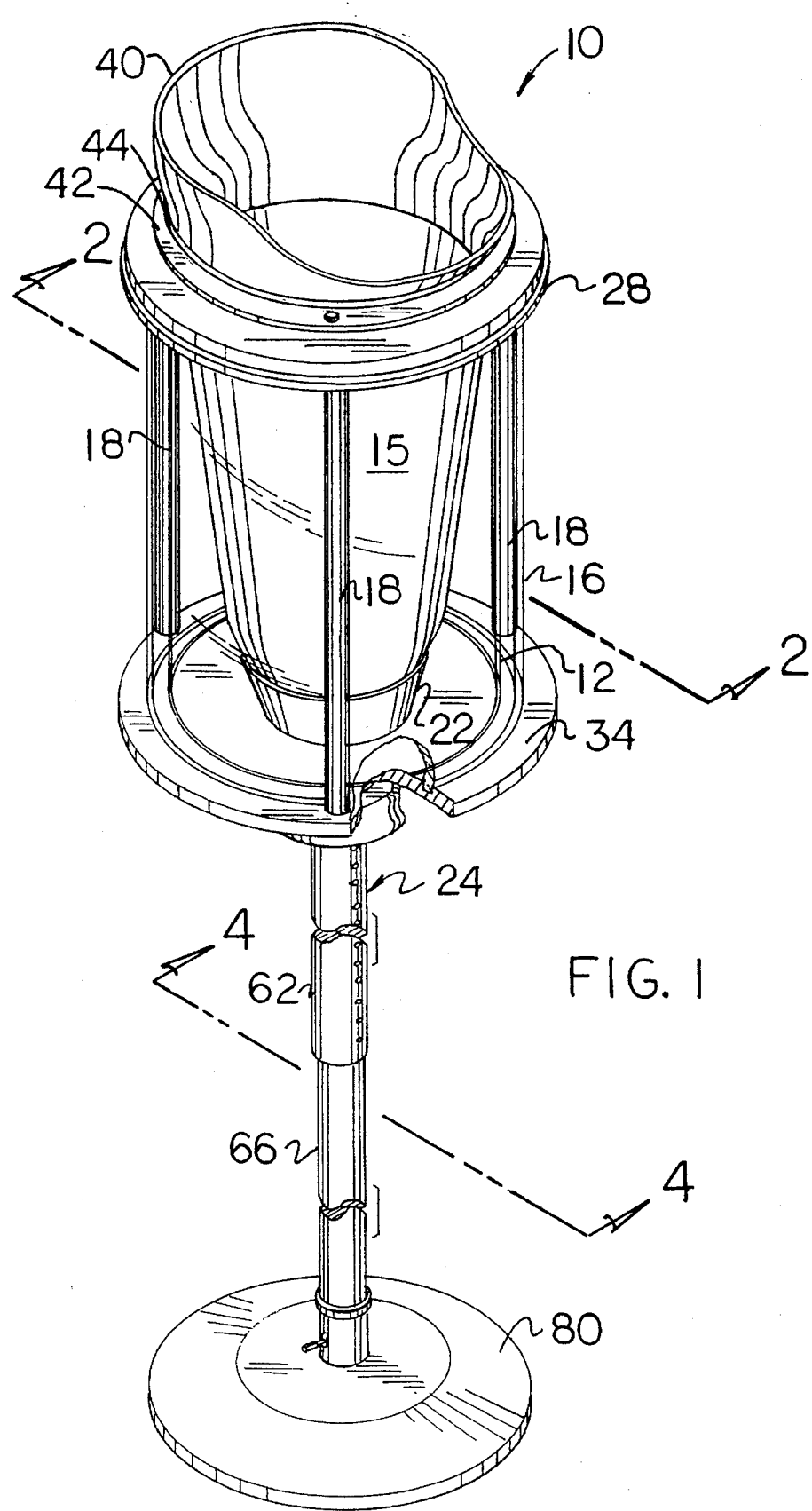
FIG. 1 is a perspective view of the novel machine.

Referring now to FIG. 1, it will there be seen that an illustrative embodiment of the invention is denoted as a whole by the reference numeral 10.

As perhaps best understood in connection with FIG. 2, prosthetic casting machine 10 includes bladder 12 of flexible, cylindrical configuration for ensleeving a liner 14 that receives the stump, not shown, of an amputee. The prothetist places a layer of plaster 15 that is about one-eighth of an inch in thickness into overlying relation to liner 14 before the stump and liner are inserted into machine 10. Note that bladder 12 is spaced radially outwardly from liner 14 in concentric relation thereto. Moreover, note that bladder 12 is preferably transparent, and that liner 14 is preferably made of a transparent silicone.

Cylinder 16 concentrically ensleeves bladder 12, said cylinder being spaced radially outwardly of said bladder when said bladder is ensleeved thereby. In a preferred embodiment, cylinder 16 is made of a strong, clear material such as polycarbonate plastic.

A rigid frame means engages the uppermost and lowermost ends of bladder 12 and cylinder 16; in a preferred embodiment, said frame means is provided in part by a plurality of equidistantly and circumferentially spaced apart stay rods, collectively denoted 18, that are disposed radially around cylinder 16 in concentrically disposed relation thereto.

Valve means 19 enables introduction of a gaseous fluid into cylindrical space 21 between bladder 12 and cylinder 16. In a preferred embodiment, an air compressor, not shown, supplies air at a pressure of between two to six pounds per square inch; this ensures that bladder 12 will be uniformly pressed against plaster 15. A vacuum pump, also not shown, is employed for evacuating air from said cylindrical space through said valve means 19.

Rigid bottom support plate 20 is disposed at the lowermost end of the frame means.

Centrally apertured distal rest plate 22 is positioned below the lowermost end of liner 14; when the patient inserts his or her stump into machine 10, said lowermost end of liner 14 is supported by said distal rest plate 22. Note that boss 14a at the lowermost end of liner 14 extends into said central aperture.

Figure 4:
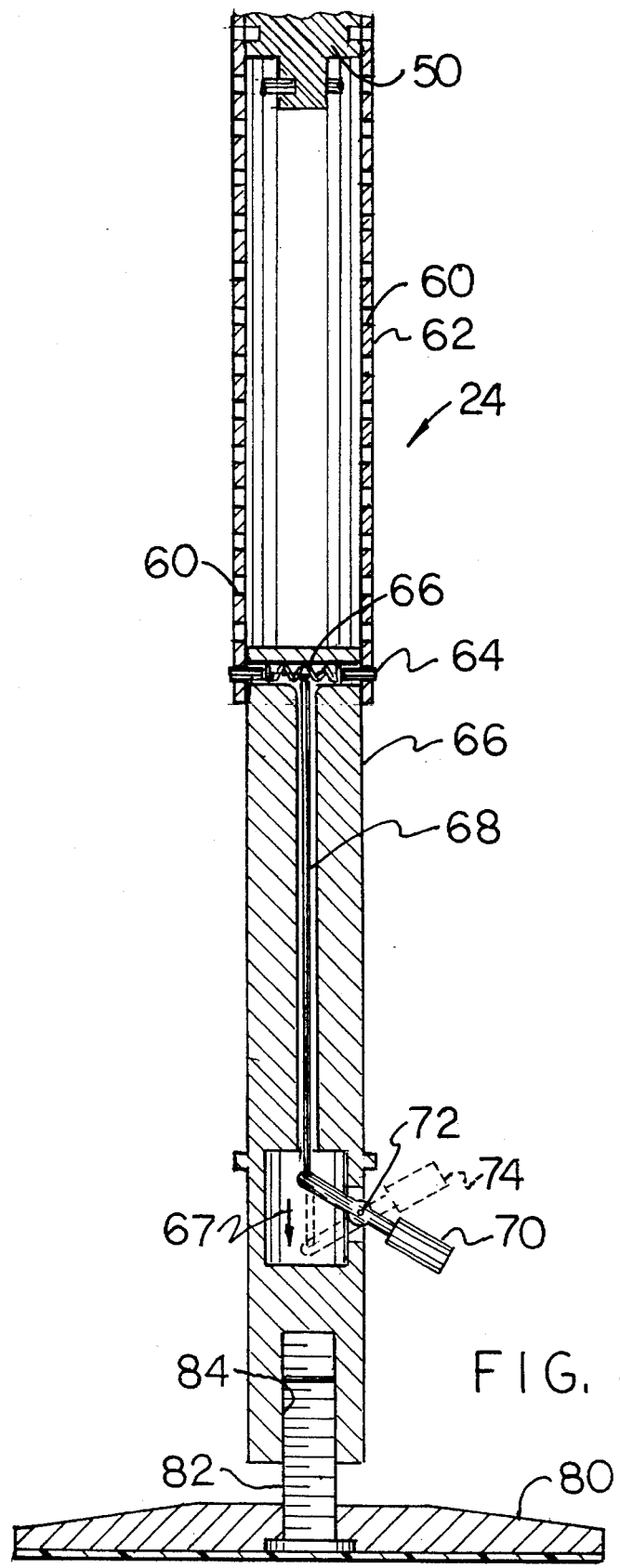
FIG. 4 is a sectional view taken along line 4—4 in FIG. 1.

Rigid, upstanding leg means, denoted 24 as a whole in FIGS. 1 and 4, supports said bottom support plate 20 and hence the entire frame means.

Accordingly, a plaster-covered liner receiving a patient's stump is supported by distal rest plate 22 and said leg means 24 so that a uniform pressure is applied to said plaster and liner upon introduction of said gaseous fluid into space 21 between bladder 12 and cylinder 16 so that the stump is under load when pressure is applied so that the novel machine produces a hard socket matching the contour of the patient's stump under load.

The rigid frame assembly further includes an upper assembly and a lower assembly for engaging opposite ends of bladder 12, cylinder 16, and stay rods 18. More particularly, as best depicted in FIG. 2, the upper assembly includes an upper mounting ring 26 of annular configuration and an upper clamping ring 28 of annular configuration that surmounts said upper mounting ring.

Bladder 12 has a radially outwardly extending upper flange 30 at an upper end thereof, and said upper flange 30 is clamped between upper mounting ring 26 and said upper clamping ring 28. Similarly, bladder 12 has a radially outwardly extending lower flange 32 at a lower end thereof, and said lower flange is clamped between bottom support plate 20 and lower mounting ring 34.

Note that upper mounting plate 26 and lower mounting plate 34 each have an annular groove formed therein for receiving opposite ends of cylinder 16, and that said plates 26 and 34 each have a plurality of circumferentially spaced countersunk bores formed therein for receiving opposite ends of stay rods 18, and that upper clamping plate 28 and lower support plate 20 provide means for closing outermost ends of said bores when said stay rods are disposed therewithin.

Brim means 40 receives a stump amputated above a knee. Interconnecting means for interconnecting brim means 40 and liner 14 includes annular sealing plate 42 that surmounts and overlies upper clamping ring 28, said upper clamping ring having an annular recess formed therein along its inner periphery, an annular resilient gasket 44 being received within said annular recess, and said annular sealing plate 42 overlying an outermost periphery of said gasket to retain said gasket in said recess, said brim means 40 being snugly received within said gasket and said brim means being secured by suitable means such as an adhesive to an exterior surface of said liner 14.

A "suck back" assembly 50, disclosed in FIGS. 2 and 3, enables the prosthetist to extend the stump axially at the distal end of the liner. Slide member 50 is slideably received within leg means 24, and is movable between a raised or extended and a lowered or retracted position as depicted in FIGS. 2 and 3, respectively. A locking means selectively locks slide member 50 into its raised and lowered positions. Note in FIG. 2 that the leading end of slide member 50 is flush with the bottom of distal rest plate 22 and abuts boss 14a of liner 14 when slide member 50 is in its raised position. This is the repose position of liner 14. The locking means includes a vertically spaced apart pair of annular grooves or bores 51, 53 formed in said slide member 50, a radially disposed pin 54 having a radially innermost end thereof selectively engageable with said annular grooves, and a handle 56 positioned at a radially outermost end of said pin so that radially outwardly directed retraction of said pin disengages said pin and said grooves so that slide member 50 may be displaced either up or down, and wherein radially inwardly directed insertion of pin 54 locks slide member 50 into a preselected lowered or raised position. A handle, not shown, enables displacement of slide member 50 when pin 54 is retracted.

The fleshy end of a residual limb is deformed and extended in an axial direction when slide member 50 is moved from its extended to its retracted position; plaster 10 sets while the stump is elongated. Accordingly, the hard socket will have excess space at its distal end when the stump is in its at repose, i.e., unelongated or natural condition. In other words, the stump elongation enables the subsequent manufacturing of a hard socket having a thickened distal end.

Leg means 24, best disclosed in FIG. 4, is of telescopic construction so that machine 10 may accommodate individuals of varying heights. Leg means 24 includes a coarse adjustment means for adjusting said leg means roughly to an individual's height, and fine adjustment means for adjusting the coarse adjustment so that the machine may be precisely fitted to an individual's height.

The coarse adjustment means includes a plurality of vertically spaced apart adjustment holes, collectively denoted 60, formed in a first telescopic housing 62 and a biased detent means 64 carried in a second telescopic housing 66 that is slideably received within said first telescopic housing 62, said biased detent means 64 being selectively engageable with said adjustment holes 60 to vary the relative extension of said second telescopic means 66 with respect to said first telescopic means 62.

More particularly, detent means 64 includes a pair of detents as shown, and a bias means 66 urges them radially outwardly into their respective locking positions. Elongate rod 68 is disposed in a bore coincident with the longitudinal axis of symmetry of leg means 24 as shown, and when displaced downwardly as at 67 by pivoting handle 70 about pivot point 72 to position 74, said detents 64 are retracted to allow telescopic displacement of legs 62, 66. Upon release of handle 70, bias means 66 returns to its position of repose, and detents 64 are again extended.

The fine adjustment means includes a flat base member 80 adapted to overlie a support surface that supports said machine, a screw member 82 secured to said flat base member, said screw member projecting upwardly from said flat base member, and said second telescopic leg means having a solid lowermost end having a screw-receiving, internally threaded bore means 84 formed therein to screw-threadedly receive said screw member. Thus, rotation of base 80 and hence screw 82 varies the displacement between flat base member 80 and second telescopic leg 66.

With this apparatus, a prothetist can fashion a hard socket while the patient is standing with his or her residual limb positioned in the machine as aforesaid. Since the stump is under load at the time of prosthesis fabrication, the prosthesis will fit better and provide greater comfort than those prostheses made in the absence of a load. The stump elongation procedure herein disclosed will insure that clearance space will exist between the distal end of the residual limb and the distal end of the hard socket produced by the novel machine.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A prosthetic nonmanual molding casting machine, comprising:

a flexible liner for receiving a stump of an amputee, said flexible liner having an open top end and a closed distal end;

a layer of plaster disposed in overlying relation to an outer surface of said liner;

a bladder of flexible, cylindrical configuration for receiving said flexible plaster-covered liner said bladder being concentrically disposed relative to said liner;

a cylinder for receiving said bladder, said cylinder being concentrically disposed relative to said bladder;

rigid frame means for engaging uppermost and lowermost ends of said bladder and cylinder;

means for introducing a gaseous fluid into a cylindrical space between said bladder and said cylinder; to displace said bladder radially inwardly into overlying relation to said layer of plaster;

means for evacuating a gaseous fluid from said cylindrical space;

a lower support plate disposed at a lowermost end of said rigid frame means, said lower support plate being rigid;

a centrally-apertured distal rest plate for supporting a distal end of said plaster-covered liner, said distal rest plate being supported by said lower support plate;

a rigid, upstanding leg means for supporting said lower support plate;

whereby said plaster-covered liner receiving a patient's stump is supported by said distal rest plate and said leg means so that a uniform pressure is applied to said plaster-covered liner upon introduction of said gaseous fluid into said space between said cylinder and said bladder;

whereby said stump is under load when said pressure is applied so that said machine produces a hard socket matching the contour of the stump under load.

2. The machine of claim 1, wherein said rigid frame means includes a plurality of circumferentially spaced stay rod means spaced radially around said cylinder in concentric relation thereto for supporting a patient's weight.

3. The machine of claim 2, wherein said rigid frame assembly further includes an upper assembly and a lower assembly for engaging opposite ends of said bladder, said cylinder, and said stay rods.

4. The machine of claim 3, wherein said upper assembly includes an upper mounting ring of annular configuration and an upper clamping ring of annular configuration that surmounts said upper mounting ring.

5. The machine of claim 4, wherein said bladder has a radially outwardly extending upper flange at an upper end thereof, and wherein said upper flange is clamped between said upper clamping ring and said upper mounting ring.

6. The machine of claim 5, wherein said lower assembly includes said lower support plate and a lower mounting ring that overlies said lower support plate, wherein said bladder has a radially outwardly extending lower flange at a lower end thereof, and wherein said lower flange is clamped between said lower support plate and said lower mounting ring.

7. The machine of claim 6, wherein said upper mounting plate and said lower mounting plate each have an annular groove formed therein for receiving opposite ends of said cylinder.

8. The machine of claim 7, wherein said upper mounting plate and said lower mounting plate each have a plurality of circumferentially spaced countersunk bores formed therein for receiving opposite ends of said stay rods, and wherein said upper clamping plate and said lower support plate provide means for closing outermost ends of said bores when said stay rods are disposed therewithin.

9. The machine of claim 8, further comprising a brim means for receiving a stump amputated above a knee, and further comprising interconnecting means for interconnecting said brim means and said liner ensleeved within said bladder.

10. The machine of claim 9, wherein said interconnecting means includes an annular sealing plate that surmounts and overlies said upper clamping ring, said upper clamping ring having an annular recess formed therein along its inner periphery, a resilient gasket being received within said annular recess, and said annular sealing plate overlying an outermost periphery of said gasket to retain said gasket in said recess, said brim means being snugly received within said gasket and said brim means being secured to an interior surface of said liner.

11. The machine of claim 1, further comprising a slide member having a lower, retracted position and having a raised, extended position, said slide member being slideably disposed within an uppermost end of said leg means, and said slide member abutting a lowermost end of said plaster-covered liner through said central aperture in said distal rest plate.

12. The machine of claim 11, wherein said slide member has a leading end that is flush with a lowermost end of said plaster-covered liner when said slide member is in its extended position and that supports a fleshy part of a distal end of said stump when in said extended position, said fleshy part being sucked axially downward when said slide member is displaced from its extended to its retracted position.

13. The machine of claim 12, further comprising locking means for selectively locking said slide member into its extended and retracted positions.

14. The machine of claim 13, wherein said locking means includes a vertically spaced apart pair of annular grooves formed in said slide member, a radially disposed pin having a radially innermost end thereof selectively engageable with said annular grooves, and a handle positioned at a radially outermost end of said pin so that radially outwardly directed retraction of said pin disengages said pin and said grooves so that said slide member may be retracted or extended, and wherein radially inwardly directed insertion of said pin locks said slide member into a preselected retracted or extended position.

15. The machine of claim 1, wherein said leg means is of telescopic construction so that said machine accommodates individuals of varying heights.

16. The machine of claim 15, wherein said leg means includes coarse adjustment means for adjusting said leg means roughly to an individual's height, and fine adjustment means for adjusting said coarse adjustment so that said machine may be precisely fitted to an individual's height.

17. The machine of claim 16, wherein said coarse adjustment means includes a plurality of vertically spaced apart adjustment holes formed in a first telescopic leg and a biased detent means carried in a second telescopic leg that is slideably received within said first telescopic leg, said biased detent means being selectively engageable with said adjustment holes to vary the relative extension of said second telescopic leg with respect to said first telescopic leg.

18. The machine of claim 17, wherein said fine adjustment means includes a flat base member adapted to overlie a support surface that supports said machine, a screw member secured to said flat base member, said screw member projecting upwardly from said flat base member, and said second telescopic leg having a solid lowermost end having a screw-receiving, internally threaded bore formed therein to screw-threadedly receive said screw member, whereby rotation of said screw member varies the displacement between said flat base member and said second telescopic leg.

19. The machine of claim 1, wherein said bladder is made of a transparent silicone.

20. The machine of claim 1, wherein said cylinder is made of a transparent material.

* * * * *